United States Patent [19]

Katsumata et al.

[11] Patent Number: 5,563,052

[45] Date of Patent: Oct. 8, 1996

[54] PROCESS FOR PRODUCING L-TRYPTOPHAN

[75] Inventors: Ryoichi Katsumata, Machida; Masato Ikeda, Sagamihara, both of Japan

[73] Assignee: Kyowa Hakko Kogyo Co., LTD, Tokyo, Japan

[21] Appl. No.: 245,823

[22] Filed: May 18, 1994

Related U.S. Application Data

[63] Continuation of Ser. No. 913,779, Jul. 14, 1992, abandoned, which is a continuation of Ser. No. 337,176, Apr. 12, 1989, abandoned.

[30] Foreign Application Priority Data

Apr. 18, 1988 [JP] Japan .................................. 63-93540

[51] Int. Cl.$^6$ .................... C12P 13/72; C12N 15/63; C12N 15/77
[52] U.S. Cl. ............... 435/108; 435/232.32; 435/320.1; 435/29; 435/60; 435/72
[58] Field of Search .................. 435/69.1, 71.2, 435/172.3, 108, 252.3, 252.32, 320.1; 536/27.1

[56] References Cited

FOREIGN PATENT DOCUMENTS

| | | |
|---|---|---|
| 0136359 | 4/1986 | European Pat. Off. . |
| 0183175 | 6/1986 | European Pat. Off. . |
| 61-149082 | 7/1986 | Japan . |
| 62-79775 | 4/1987 | Japan . |
| 62-244382 | 10/1987 | Japan . |

OTHER PUBLICATIONS

Shiio, I. et. al., Agric. Biol. Chem., vol. 46, No. 7 (1982) pp. 1849–1854.
Sugimoto, S. and Shiio, I., Agric. Biol. Chem., vol. 49, vol. 1 (1985) pp. 39–48.
Patent Abstracts of Japan, vol. 10, No. 345 (1986) p. 2401.
E. Tribe & J. Pittard, 1979, "Hyperproduction of Tryptophan by *Escherchia coli*: Genetic Manipulation of the Pathways Leading to Tryptophan Formulation", Applied & Environmental Microbiology, vol. 38, pp. 181–190.
S. Aiba et al., 1982, "New Approach to Tryptophan Production by *Eschericha coli*: Genetic Manipulation of Composite Plasmids In Vitro", Applied & Environmental Microbiology, vol. 43, pp. 289–297.

*Primary Examiner*—Robert A. Wax
*Assistant Examiner*—William W. Moore
*Attorney, Agent, or Firm*—Fitzpatrick Cella Harper & Scinto

[57] ABSTRACT

L-tryptophan is produced by constructing a recombinant DNA composed of a vector DNA and DNA fragments bearing all of genetic information relating to the synthesis of DS, AS, PRT, PRAI, InGPS and TS, introducing the recombinant DNA in a microorganism belonging to the genus *Corynebacterium* or *Brevibacterium*, culturing the microorganism in a medium, and recovering L-tryptophan accumulated in the culture.

5 Claims, 1 Drawing Sheet

FIG. 1

PROCESS FOR PRODUCING L-TRYPTOPHAN

This application is a continuation, of application Ser. No. 07/913,779, filed Jul. 14, 1992, now abandoned, which is a continuation of application Ser. No. 07/337,176, filed Apr. 12, 1989, now abandoned.

BACKGROUND OF THE INVENTION

Various strains belonging to the genus *Corynebacterium* or *Brevibacterium* and being capable of producing L-tryptophan have been constructed by recombinant DNA technology. They include strains carrying a recombinant DNA that contains a gene coding for anthranilate synthase (hereinafter abbreviated to AS) [Japanese Published Unexamined Patent Application No. 156292/1984 (European Publication No. 136359)], strains carrying a recombinant DNA that contains genes coding for anthranilate phosphoribosyl transferase (hereinafter abbreviated to PRT), N-5'-phosphoribosyl anthranilate isomerase (hereinafter abbreviated to PRAI), indole-3-glycerol phosphate synthase (hereinafter abbreviated to InGPS) and tryptophan synthase (hereinafter abbreviated to TS) (Japanese Published Unexamined Patent Application No. 149082/1986), strains carrying a recombinant DNA that contains a gene coding for 3-deoxy-D-arabino-hepturosonate-7-phosphate synthase (hereinafter abbreviated to DS) [Japanese Published Unexamined Patent Application No. 51980/1987 (European Publication No. 183175)] (said genes being hereinafter referred to as AS gene, PRT gene, PRAI gene, InGPS gene, TS gene and DS gene respectively, in some cases), and strains carrying a recombinant DNA that contains PRAI-InGPS gene (Japanese Published Unexamined Patent Application No. 79775/1987).

With the increasing demand for L-tryptophan in recent years, improvement in the process for producing this amino acid has been desired. As a result of intensive studies to construct a new strain with higher L-tryptophan productivity by recombinant DNA technology, it has been found that L-tryptophan productivity can be increased by introducing into a strain belonging to the genus *Corynebacterium* or *Brevibacterium* a recombinant DNA containing DNA fragments bearing all of genetic information relating to the synthesis of DS, AS, PRT, PRAI, InGPS and TS, and the present invention has been accomplished. As stated above, L-tryptophan-producing strains carrying a recombinant plasmid DNA that contains genes relating to the biosynthesis of L-tryptophan, i.e. AS, PRT, PRAI, InGPS and TS genes (Japanese Published Unexamined Patent Application Nos. 156292/1984, 149082/1986 and 79775/1987), and those carrying a recombinant plasmid DNA that contains DS gene (Japanese Published Unexamined Patent Application No. 51980/1987) have been known. However, no example has been known which employs a recombinant DNA containing all of DS, AS, PRT, PRAI, InGPS and TS genes. The fact that L-tryptophan productivity can be further increased by simultaneous amplification of all of these genes has been first disclosed in the present invention.

SUMMARY OF THE INVENTION

The present invention relates to a process for producing L-tryptophan which comprises culturing in a medium a microorganism belonging to the genus *Corynebacterium* or *Brevibacterium* and carrying a recombinant DNA composed of a vector DNA and DNA fragments, allowing L-tryptophan to accumulate in the culture, and recovering L-tryptophan therefrom, said DNA fragments bearing all the genes relating to the synthesis of DS, AS, PRT, PRAI, InGPS and TS. Thus the present invention is related to the industrial field of bioindustry, particularly to the manufacture of L-tryptophan which is a useful substance in the pharmaceutical and animal feed industries.

DETAILED DESCRIPTION OF THE INVENTION

The present invention provides a process for producing L-tryptophan which comprises culturing in a medium a microorganism belonging to the genus *Corynebacterium* or *Brevibacterium* and carrying a recombinant DNA composed of a vector DNA and DNA fragments bearing all of genetic information relating to the synthesis of DS, AS, PRT, PRAI, InGPS and TS, allowing L-tryptophan to accumulate in the culture, and recovering L-tryptophan therefrom.

As the DNA fragments, those derived from microorganisms belonging to the genus *Corynebacterium* or *Brevibacterium* may be used.

As the donor strains of the individual genes, any microorganisms which are prototrophic in the biosynthesis of aromatic amino acids may be used. Particularly preferred genes are those originated from procaryotes such as bacteria belonging to the genus *Escherichia*, *Corynebacterium* or *Brevibacterium*, and those originated from aromatic amino acid-producing mutants derived from such bacteria are the most preferred.

Any of the strains known as glutamic acid-producing coryneform bacteria may be used as the host microorganism belonging to the genus *Corynebacterium* or *Brevibacterium*. Preferred strains are listed below.

*Corynebacterium glutamicum* ATCC 13032

*Corynebacterium acetoacidophilum* ATCC 13870

*Corynebacterium herculis* ATCC 13868

*Corynebacterium lilium* ATCC 15990

*Corynebacterium melassecola* ATCC 17965

*Brevibacterium divaricatum* ATCC 14020

*Brevibacterium flavum* ATCC 14067

*Brevibacterium immariophilium* ATCC 14068

*Brevibacterium lactofermentum* ATCC 13869

*Brevibacterium thiogenitalis* ATCC 19240

Aromatic amino acid-producing mutants derived from the above strains by mutation are more preferably used. These mutants can be obtained as strains having amino acid-requirement and/or resistance to amino acid analogues [J. Agric. Chem. Soc., 50(1), p.R 79 (1976)].

As the vector for inserting said DNA fragments, any plasmid that is autonomously replicable in microorganisms belonging to the genus *Corynebacterium* or *Brevibacterium* may be used. Examples of such plasmids are pCG1 [Japanese Published Unexamined Patent Application No. 134500/

1982 (European Patent No. 58889, U.S. Pat. No. 4,617, 267)], pCG2 [Japanese Published Unexamined Patent Application No. 35197/1983 (European Patent No. 73062, U.S. Pat. No. 4,489,160)], pCG4 and pCG11 [Japanese Published Unexamined Patent Application No. 183799/1982 (European Patent No. 63763, U.S. Pat. No. 4,500,640)], pCE54 and pCB101 [Japanese Published Unexamined Patent Application No. 105999/1983 (European Publication No. 82485, U.S. Pat. No. 4,710,471)], and pCE51, pCE52 and pCE53 [Mol. Gen. Genet., 196, 175 (1984)].

A recombinant DNA composed of a vector DNA and a donor DNA containing a gene coding for DS can be obtained as a mixture with various recombinant DNAs according to the ordinary methods, for example, by cleaving the donor DNA and the vector DNA with suitable restriction enzymes followed by, if necessary, treatment of the cleaved ends with a terminal transferase or DNA polymerase, and ligating both DNAs by the action of DNA ligase [Methods in Enzymology, 68 (1979)]. The mixture of ligated DNAs thus obtained is used to transform a mutant strain of the genus *Corynebacterium* or *Brevibacterium* deficient in DS gene, and a transformant in which the deficiency is complemented is selected. The recombinant DNA containing the DS gene can be obtained by isolating the plasmid from the transformant obtained above. Transformation of a strain of the genus *Corynebacterium* or *Brevibacterium* can be carried out by the method using protoplasts [Japanese Published Unexamined Patent Application No. 186492/1982 (European Publication No. 63764, U.S. Pat. No. 4,683,205) and Japanese Published Unexamined Patent Application No. 186489/1982 (European Patent No. 64680, U.S. Pat. No. 4,681,847)].

A recombinant DNA composed of a vector DNA and a donor DNA containing the genes relating to the biosynthesis of L-tryptophan can be obtained in a similar manner; that is, by transforming a tryptophan-requiring mutant of the genus *Corynebacterium* or *Brevibacterium* deficient in any one of the genes relating to the L-tryptophan biosynthesis with a mixture of recombinant DNAs composed of the chromosomal DNA and the vector DNA, and selecting a transformant having no L-tryptophan requirement, followed by isolation of the recombinant DNA from the transformant. The genes relating to the L-tryptophan biosynthesis can be identified by a complementation test using defined L-tryptophan-requiring routants derived from a microorganism of the genus *Corynebacterium*, *Brevibacterium* or *Escherichia*. It was demonstrated by the test that, in *Corynebacterium glutamicum*, all of genetic information relating to the synthesis of AS, PRT, PRAI, InGPS and TS, which are the enzymes relating to the biosynthesis of L-tryptophan, was located on the BamHI DNA fragment of 11.0 kilobases (Kb) [Example (3)].

Recombination of the DNA fragment containing the DS gene and the DNA fragment containing the genes relating to the L-tryptophan biosynthesis obtained above gives a recombinant DNA containing both of the genes. These genes can be amplified simultaneously by introducing the recombinant DNA thus obtained into a host microorganism. Alternatively, these genes can also be amplified, if they are contained in different vector plasmids capable of coexisting in the same cell and these plasmids are simultaneously introduced in a host microorganism. In both cases, the productivity of L-tryptophan can be improved.

When the chromosomal DNA of a wild strain of the genus *Corynebacterium* or *Brevibacterium* is used as the donor in the step described above, the obtained recombinant DNA containing wild-type genes can be introduced into a microorganism belonging to the genus *Corynebacterium* or *Brevibacterium* through transformation. However, it is known that, in microorganisms of the genus *Corynebacterium* or *Brevibacterium*, DS is subject to feedback inhibition by phenylalanine and tyrosine, and AS and PRT are subject to feedback inhibition by tryptophan [Agric. Biol. Chem., 39, 351 (1975); ibid., 47, 2295 (1983)]. Hence, it is preferable to use a recombinant DNA containing mutant genes coding for DS, AS and PRT free from such feedback inhibition in order to ensure higher L-tryptophan productivity in a microorganism of the genus *Corynebacterium* or *Brevibacterium*. The mutant DS, AS and PRT genes are obtained by using as a donor the chromosomal DNA of a mutant strain of the genus *Corynebacterium* or *Brevibacterium* whose DS, AS or PRT is free from feedback inhibition. Selection of the mutant genes can be carried out based on complementation of DS, AS or PRT deficiency as described above. Alternatively, such mutant DS, AS and PRT genes can be obtained by using, as a recipient, a strain of the genus *Corynebacterium* or *Brevibacterium* containing wild-type DS gene or wild-type AS and PRT genes, and by selecting a transformant resistant to a phenylalanine analogue such as p-fluorophenylalanine (hereinafter abbreviated to PFP) or a tryptophan analogue such as 5-fluorotryptophan (hereinafter abbreviated to 5FT). The recombinant DNA containing the mutant DS, AS and PRT genes can be prepared in the same manner as in the-preparation of the recombinant DNA containing the wild-type genes. Alternatively, such a recombinant DNA may be prepared by in vitro mutagenesis of the recombinant DNA containing the wild-type genes according to the method described in Mol. Gen. Genet, 145, 101 (1978), or by in vivo mutagenesis of a strain carrying the recombinant DNA containing the wild-type genes according to a conventional method. The recombinant DNA containing the wild-type or mutant DS gene and the wild-type or mutant genes relating to the L-tryptophan biosynthesis can be introduced into a strain of the genus *Corynebacterium* or *Brevibacterium* by the transformation method using protoplasts mentioned above.

Production of L-tryptophan by the use of such a transformant carrying the recombinant plasmid can be carried out by the same method as in a conventional process for producing an amino acid by fermentation. The transformant is cultured in an ordinary culture medium containing carbon sources, nitrogen sources, inorganic substances, amino acids, vitamins and other nutrients under aerobic conditions at a controlled temperature, pH, etc., and L-tryptophan accumulated in the culture is recovered therefrom.

As the carbon sources, various carbohydrates such as glucose, glycerol, fructose, sucrose, maltose, mannose, starch, starch hydrolyzate and molasses; polyalcohols; and various organic acids such as pyruvic acid, fumaric acid, lactic acid and acetic acid may be used. Hydrocarbons and alcohols may also be used depending on the assimilability of the strain employed. Particularly, cane molasses is preferably used.

As the nitrogen sources, ammonia; various inorganic and organic ammonium salts such as ammonium chloride, ammonium sulfate, ammonium carbonate and ammonium acetate; urea and other nitrogen-containing substances; and nitrogen-containing organic substances such as peptone, NZ-amine, meat extract, yeast extract, corn steep liquor, casein hydrolyzate, fish meal or its digested product, and chrysalis hydrolyzate may be used.

As the inorganic substances, dipotassium hydrogen phosphate, potassium dihydrogen phosphate, ammonium sulfate, ammonium chloride, magnesium sulfate, sodium chloride, ferrous sulfate, manganese sulfate, calcium carbonate, etc.

may be used. Amino acids and vitamins such as biotin and thiamine may also be added as required depending on the carbon and nitrogen sources in the medium used. In addition, when the strain used requires a specific substance for the growth, it is necessary to add the substance to the medium.

Cultivation is carried out under aerobic conditions, for example, by shaking culture or by aeration-stirring culture, preferably at a temperature in the range of 20° to 40° C. The pH of the medium is preferably maintained around neutrality during the cultivation. L-tryptophan is accumulated in the medium usually by culturing for one to five days. After the completion of cultivation, the cells are removed from the culture by filtration or centrifugation and the filtrate or supernatant thus separated is treated in a known manner (e.g., treatment with activated carbon and ion-exchange resins) to recover L-tryptophan.

L-tryptophan can thus be produced in higher yields by using a strain of the genus *Corynebacterium* or *Brevibacterium* carrying a recombinant DNA that contains the DS gene and the genes relating to the biosynthesis of L-tryptophan.

In the present specification, there is shown a case where the productivity of L-tryptophan is increased by introducing a recombinant DNA containing all of the DS, AS, PRT, PRAI, InGPS and TS genes into *Corynebacterium glutamicum*. However, the intended object can also be attained by using any other glutamic acid-producing coryneform bacteria in place of *Corynebacterium glutamicum*.

In spite of many common microbiological properties, so called glutamic acid-producing coryneform bacteria having high glutamic acid productivity are classified to various species by researchers and even to different genera such as *Corynebacterium* and *Brevibacterium* probably because of their industrial importance. However, it has been pointed out that these microorganisms should be classified as one species because they have homology in the amino acid composition of cell walls and the base composition of DNA. Further, it has been reported that these microorganisms have more than 70–80% homology in DNA-DNA hybridization, indicating that the microorganisms are very closely related [refer to Komatsu, Y.: Report of the Fermentative Research Institute, No. 55, 1 (1980), and Suzuki, K., Kaneko, T., and Komagata, K.: Int. J. Syst. Bacteriol., 31, 131 (1981)]. Considering the above-mentioned very close relationship of glutamic acid-producing microorganisms, it is readily assumed that the present invention is applicable to all of the glutamic acid-producing coryneform bacteria. The applicability of the present invention depends on whether the recombinant DNA is autonomously replicable in the glutamic acid-producing coryneform bacteria and whether the DS gene and the genes relating to the L-tryptophan biosynthesis are expressed therein, and so slight differences in DNA homology among the glutamic acid-producing coryneform bacteria are negligible. It is apparent that the glutamic acid-producing coryneform bacteria have the common function to allow replication of plasmids and expression of genes from the fact that plasmid pCG4 which is isolated from *Corynebacterium glutamicum* 225–250 [Japanese Published Unexamined Patent Application No. 183799/1982 (European Patent No. 63763, U.S. Pat. No. 4,500,640)] and which has spectinomycin and/or streptomycin resistance gene(s) can be replicated and the gene(s) can be expressed in glutamic acid-producing coryneform bacteria such as strains of the genera *Corynebacterium* and *Brevibacterium* [Japanese Published Unexamined Patent Application No. 186492/1982 (European Publication No. 63764, U.S. Pat. No. 4,683,205)]. Therefore, the process of the present invention for constructing an L-tryptophan-producing microorganism by introducing a recombinant DNA containing all of the DS, AS, PRT, PRAI, InGPS and TS genes is applicable not only to *Corynebacterium glutamicum*, but also to all the glutamic acid-producing coryneform bacteria including the bacteria of the genera *Corynebacterium* and *Brevibacterium*.

A certain specific embodiment of the present invention is illustrated by the following representative example.

EXAMPLE

Production of L-tryptophan by a strain carrying a recombinant plasmid that contains DS gene of *Corynebacterium glutamicum* K38 and all of the genes relating to the synthesis of AS, PRT, PRAI, InGPS and TS of *Corynebacterium glutamicum* K55

(1) Preparation of chromosomal DNAs of *Corynebacterium glutamicum* K38 (FERM BP-454) and *Corynebacterium glutamicum* K55 (FERM BP-864) and vector plasmids pCE53 and pCG116:

*Corynebacterium glutamicum* K38 (FERM BP-454), which is resistant to PFP and p-aminophenylalanine, and *Corynebacterium glutamicum* K55 (FERM BP-864), which is requiring phenylalanine and tyrosine and resistant to 5-methyltryptophan, tryptophan hydroxamate, 6-fluorotryptophan, 4-methyltryptophan, PFP, p-aminophenylalanine, tyrosine hydroxamate and phenylalanine hydroxamate, were respectively cultured in NB medium (20 g/l bouillon powder and 5 g/l yeast extract; pH 7.2). The resulting seed cultures (20 ml each) were respectively inoculated into 400 ml of semi-synthetic medium SSM [20 g/l glucose, 10 g/l $(NH_4)_2SO_4$, 3 g/l urea, g/l yeast extract, 1 g/l $KH_2PO_4$, 0.4 g/l $MgCl_2.6H_2O$, 10 mg/l $FeSO_4.7H_2O$, 0.2 mg/l $MnSO_4.4-6H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 µg/l biotin and 1 mg/l thiamine hydrochloride; pH 7.2] containing 100 µg/ml each of phenylalanine and tyrosine, and were cultured with shaking at 30° C. The optical density (OD) at 660 nm (hereinafter the optical density is measured at 660 nm unless otherwise specified) was determined with a Tokyo Koden colorimeter, and when the OD reached 0.2, penicillin G was added to a concentration of 0.5 unit/ml. Culturing was further continued until OD reached 0.6.

Figure 1:
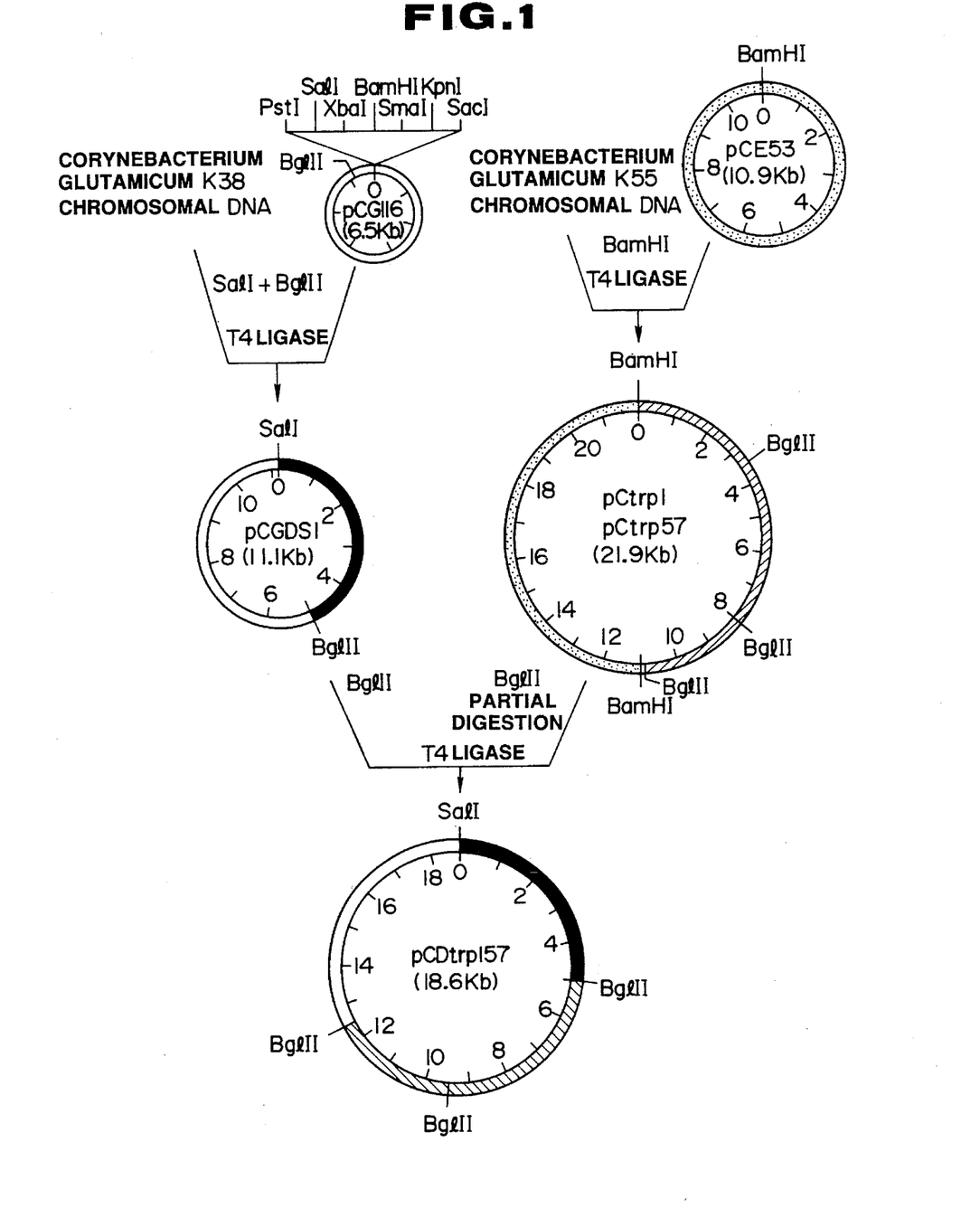
FIG. 1 shows the cleavage map of pCDtrp157 for restriction enzymes, and the steps for constructing the plasmid. The DS gene is contained in the parts indicated by the thick solid line of pCDtrp157, while the genes relating to the L-tryptophan biosynthesis are contained in the shaded parts of pCDtrp157. The sizes of plasmid are expressed in kilobase (Kb).

The grown cells were collected from the culture and washed with TES buffer solution [0.03M tris(hydroxymethyl)aminomethane (hereinafter abbreviated to "Tris"), 0,005M disodium ethylenediaminetetraacetate (hereinafter abbreviated to EDTA) and 0.05M NaCl; pH 8.0]. The washed cells were suspended in 10 ml of a lysozyme solution (25% sucrose, 0.1M NaCl, 0.05M Tris and 0.8 mg/ml lysozyme; pH 8.0), and subjected to reaction at 37° C. for two hours. High molecular chromosomal DNAs were isolated from the collected cells according to the method of Saito, H. and Miura, K. [Biochim. Biophys. Acta, 72, 619 (1963)].

pCE53 used as a vector is a plasmid constructed by ligating plasmid pCG1 autonomously replicable in *Corynebacterium glutamicum* with plasmid pGA22 autonomously replicable in *Escherichia coli* (refer to G. An, et al.: J. Bacteriol. 140, 400 (1979)]. It is constructed by ligating both DNAs at the BglII-cleavage site of pCGI and one of the two BamHI-cleavage sites of pGA22, which is not in the tetracycline resistance gene, utilizing the same cohesive ends. pCE53 has selection markers such as kanamycin-resistance gene derived from pGA22 and a single cleavage site for restriction enzyme BamHI.

pCG116, also used as a vector, is a plasmid constructed by ligating a linker obtained from M13mp18 RF DNA (Takara Shuzo Co., Ltd.) with the StuI-PstI-cleaved DNA fragment of pCG11 autonomously replicable in *Corynebacterium glutamicum* by utilizing their blunt ends and cohesive ends. The linker is obtained by cleaving M13mp18 RF DNA with EcoRI, repairing the cohesive ends to blunt ends with Klenow fragment (Takara Shuzo Co., Ltd.), and again cleaving the DNA with PstI. Plasmid pCG116 has a molecular size of about 6.5 Kb and a single cleavage site for each of BglII, PstI, SalI, XbaI, BamHI, SmaI, KpnI and SacI, and gives a streptomycin- and/or spectinomycin-resistance phenotype (refer to FIG. 1).

pCE53 and pCG116 were each isolated from cultured cells of *Corynebacterium glutamicum* ATCC 13032 carrying pCE53 or pCG116 according to the procedure described below.

*Corynebacterium glutamicum* ATCC 13032 carrying pCE53 or pCG116 was cultured with shaking at 30° C. in 400 ml of SSM medium and treated with penicillin G in the same manner as above, and culturing was further continued until OD reached about 0.6. The grown cells were collected, washed with TES buffer solution, and suspended in 10 ml of a lysozyme solution. The suspension was subjected to reaction at 37° C. for two hours. To the reaction mixture were successively added 2.4 ml of 5 M NaCl, 0.6 ml of 0.5 M EDTA ( pH 8.5) and 4.4 ml of a solution comprising 4% sodium laurylsulfate and 0.7M NaCl, and the resulting mixture was gently stirred and placed on ice for 15 hours. The lysate thus obtained was transferred to a centrifuge tube and subjected to centrifugation at 69,400 x g at 4° C. for 60 minutes to recover a supernatant. Then, polyethylene glycol (PEG) 6,000 (Nakarai Chemicals, Ltd.) was added thereto in an amount corresponding to 10% by weight. The mixture was gently stirred, and then placed on ice. After ten hours, the mixture was centrifuged at 1,500 xg for ten minutes to recover pellets. Then, 5 ml of TES buffer solution was added to gradually dissolve the pellets, and 2.0 ml of 1.5 mg/ml ethidium bromide was added to the solution. Cesium chloride was further added to adjust the density of the solution to 1.580.

The solution thus obtained was subjected to ultracentrifugation at 105,000 x g at 18° C. for 48 hours, and a high density band at the lower position of the centrifuge tube detected under UV irradiation was withdrawn by puncturing the side of the centrifuge tube, using a syringe, to recover the fraction containing pCE53 or pCG116 plasmid DNA. The fraction was treated five times with an equal volume of isopropanol solution [90% (V/V) isopropanol in TES buffer solution] containing a saturated amount of cesium chloride to remove ethidium bromide by extraction. Then, the solution was dialyzed against TES buffer solution.

(2) Cloning of a DNA fragment containing DS gene:

To 60 μl of reaction solution Y-100 (10 mM Tris, 6 mM MgCl$_2$ and 100 mM NaCl; pH 7.5) containing 3 μg of pCG116 plasmid DNA obtained above were added 6 units each of restriction enzymes SalI and BglII (Takara Shuzo Co., Ltd.; unless otherwise specified, restriction enzymes hereinafter used are products of Takara Shuzo Co., Ltd.), and the mixture was subjected to reaction at 37° C. for 60 minutes. The reaction was stopped by treatment with phenol. Separately, 6 units each of restriction enzymes SalI and BglII were added to 140 μl of reaction solution Y-100 containing 3 μg of the chromosomal DNA of *Corynebacterium glutamicum* K38 (FERM BP-454) obtained above, and the mixture was subjected to reaction at 37° C. for 60 minutes. The reaction was stopped by treatment with phenol.

Both reaction mixtures thus obtained were mixed, and twice as much ethanol as the mixture by volume was added to precipitate DNA. The DNA was recovered and suspended in 200 μl of water.

To 200 μl of the DNA suspension were added 40 μl of buffer solution for T4 ligase at a 10-fold concentration (660 mM Tris, 66 mM MgCl$_2$ and 100 mM dithiothreitol; pH 7.6), 40 μl of 5 mM ATP, 300 units of T4 ligase (Takara Shuzo Co., Ltd.) and 120 μl of water, and the mixture was subjected to reaction at 12° C. for 16 hours.

The reaction mixture was used for transformation of *Corynebacterium glutamicum* ATCC 13032. A seed culture of this strain (4 ml) was inoculated into 40 ml of SSM medium, and cultured with shaking at 30° C. When OD reached 0.2, the culture was treated with penicillin G in the same manner as in (1) above, and culturing was further continued until OD reached 0.6. The grown cells were collected and suspended to a concentration of about $10^9$ cells per milliliter in 10 ml of RCGP medium [5 g/l glucose, 5 g/l casamino acid, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$.7H$_2$O, 2 mg/l MnSO$_4$.4–6H$_2$O, 0.9 mg/l ZnSO$_4$.7H$_2$O, 0.04 mg/l (NH$_4$)$_6$Mo$_7$O$_{24}$.4H$_2$O, 30 mg/l biotin, 2 mg/l thiamine hydrochloride, 135 g/l disodium succinate and 30 g/l polyvinyl pyrrolidone (M.W.: 10,000); pH 7.6] containing 1 mg/ml lysozyme. The suspension was transferred to an L-type test tube and gently shaken at 30° C. for 16 hours to prepare protoplasts.

Then, 0.5 ml of the protoplast suspension was taken in a small test tube and centrifuged at 2,500 x g for five minutes to separate the protoplasts. The protoplasts were suspended in 1 ml of TSMC buffer solution (10 mM MgCl$_2$, 30 mM CaCl$_2$, 50 mM Tris and 400 mM sucrose; pH 7.5) and washed by centrifugation. The washed protoplasts were resuspended in 0.1 ml of TSMC buffer solution. Then, 100 μl of a 1:1 mixture of TSMC buffer solution at a two-fold concentration and the ligase reaction mixture obtained above was added to the protoplast suspension, and the resulting mixture was further admixed with 0.8 ml of TSMC buffer solution containing 20% PEG 6000. After three minutes, 2 ml of RCGP medium (pH 7.2) was added thereto and the resulting mixture was centrifuged at 2,500 x g for five minutes to remove a supernatant. The precipitated protoplasts were suspended in 1 ml of RCGP medium, and the suspension (0.2 ml) was spread on RCGP agar medium (RCGP medium containing 1.4% agar; pH 7.2) containing 400 μg/ml spectinomycin and cultured at 30° C. for seven days.

The colonies grown on RCGP agar medium were scraped up, and washed twice with physiological saline solution by centrifugation. The washed cells were suspended in 1 ml of physiological saline solution. The suspension was spread on minimal agar medium M1 [10 g/l glucose, 1 g/l (NH$_4$)H$_2$PO$_4$, 0.2 g/l KCl, 0.2 g/l MgSO$_4$.7H$_2$O, 10 mg/l FeSO$_4$.7H$_2$O, 0.2 mg/l MnSO$_4$.4–6H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 50 mg/l biotin, 2.5 mg/l p-aminobenzoic acid, 1 mg/l thiamine hydrochloride and 16 g/l agar; pH 7.2] containing 3 mg/ml PFP and 100 μg/ml spectinomycin. Culturing was carried out at 30° C. for five days, and transformants which are resistant to PFP and spectinomycin were selected.

Plasmid DNAs were isolated from the selected transformants in the same manner as in the isolation of pCG116 in (1) above. Digestion with various restriction enzymes and analysis by agarose gel electrophoresis revealed that the plasmid DNA isolated from one of the transformants and named pCGDS1 has a structure in which a SalI-BglII-cleaved DNA fragment of 5.0 Kb has been inserted into the SalI-BglII cleavage site on pCG116 (refer to FIG. 1).

DS activities of *Corynebacterium glutamicum* ATCC 13032 and the transformant carrying pCGDS1 were determined according to the method of P. R. Sprinavasan, D. B. Sprinson, et al. [J. Biol. Chem., 234, 716 (1959)]. It was demonstrated that DS activity of the transformant carrying pCGDS1 is 8 to 10 times as high as that of the parent strain and DS in the transformant is free from inhibition by phenylalanine and tyrosine. This indicates that the DNA fragment of 5.0 Kb introduced in pCGDS1 contains DS gene derived from *Corynebacterium glutamicum* K38.

(3) Cloning of a DNA fragment carrying all of genetic information relating to the synthesis of AS, PRT, PRAI, InGPS and TS:

To 60 µl of reaction solution Y-100 containing 3 µg of pCE53 plasmid DNA obtained in (1) above was added 6 units of restriction enzyme BamHI, and the mixture was subjected to reaction at 37° C. for 60 minutes. The reaction was stopped by heating the reaction mixture at 65° C. for 10 minutes. Separately, 6 units of restriction enzyme BamHI was added to 140 µl of reaction solution Y-100 containing 3 µg of the chromosomal DNA of *Corynebacterium glutamicum* K55 (FERM BP-864) obtained in (1) above, and the mixture was subjected to reaction at 37° C. for 60 minutes. The reaction was stopped by heating the reaction mixture at 65° C. for 10 minutes.

Both reaction mixtures thus obtained were mixed, and 40 µl of buffer solution for T4 ligase at a 10-fold concentration, 40 µl of 5 mM ATP, 300 units of T4 ligase and 120 µl of water were added to the mixture. The resulting mixture was subjected to reaction at 12° C. for 16 hours.

The reaction mixture was used for transformation of *Corynebacterium glutamicum* TA108, a strain requiring for tryptophan and lacking the gene for β-subunit of TS which has α- and β-subunits [deposited with the Fermentation Research Institute (FRI), Agency of Industrial Science and Technology, Japan under the Budapest Treaty on April 9, 1988 as FERM BP-1846].

A seed culture of TA108 strain (4 ml) was inoculated into 40 ml of SSM medium containing 50 µg/ml tryptophan, and cultured with shaking at 30° C. When OD reached 0.2, treatment with penicillin G was carried out in the same manner as in (1) above, and culturing was further continued until OD reached 0.6. The grown cells were collected and treated with lysozyme in the same manner as in (2), and the protoplasts thus obtained were subjected to transformation in the same manner as in (2) using the ligase reaction mixture prepared above. The kanamycin-resistant colonies grown on RCGP agar medium containing 200 µg/ml kanamycin were scraped up, and washed twice with physiological saline solution by centrifugation. The washed cells were suspended in 1 ml of physiological saline solution. The suspension was spread on minimal agar medium M1 containing 10 µg/ml kanamycin and cultured at 30° C. for three days, and transformants resistant to kanamycin and not requiring tryptophan were selected. From these transformants were isolated plasmid DNAs in the same manner as in the isolation of pCE53 in (1) above. Digestion with various restriction enzymes and analysis by agarose gel electrophoresis revealed that the plasmid DNA isolated from one of the transformants and named pCtrp1 has a structure in which BamHI-cleaved DNA fragment of 11.0 Kb has been inserted into the BamHI cleavage site on pCE53 (refer to FIG. 1).

The other L-tryptophan biosynthetic genes which are contained in the BamHI-cleaved DNA fragment of 11.0 Kb were identified in the following manner. pCtrp1 was used to transform *Corynebacterium glutamicum* TA105 (a strain lacking the AS gene), TA106 (a strain lacking the PRT gene) and TA107 (a strain lacking the TS-α-subunit gene) in the same manner as described above. It was demonstrated that all of the kanamycin-resistant colonies grown on RCGP agar medium containing 200 µg/ml kanamycin did not require tryptophan or growth. This indicates the presence of the AS, PRT, TS-α and TS-β genes in the above 11.0 Kb DNA fragment introduced into pCtrp1.

Separately, pCtrp1 was used to transform *Escherichia coli* ATCC 23719 (K-12, trpC⁻) according to the method of M. Dagert, et al. [Gene, 6, 23 (1979)]. It was found that all of the kanamycin-resistant colonies grown on LB agar medium (10 g/l Bacto-Tryptone, 5 g/l yeast extract, 1 g/l glucose, 5 g/l NaCl and 16 g/l agar; pH 7.2) containing 20 µg/ml kanamycin lack in requirement for tryptophan. This indicates the presence of the PRAI and InGPS genes in the above 11.0 Kb DNA fragment inserted into pCtrp1.

(4) Preparation of plasmid pCtrp57 resistant to tryptophan analogues:

TA108 strain carrying pCtrp1 was cultured in NB medium containing 10 µg/ml kanamycin till the latter stage of the logarithmic growth phase. The grown cells were collected and washed once with 50 mM Tris-maleate buffer solution (pH 6.0) by centrifugation. The washed cells were treated with 400 µg/ml N-methyl-N'-nitro-N-nitrosoguanidine in 50 mM Tris-maleate buffer solution at room temperature for 20 minutes. The treated cells were washed twice with 50 mM Tris-maleate buffer solution by centrifugation and cultured in NB medium containing 10 µg/ml kanamycin at 30° C. for 16 hours. A plasmid DNA was isolated from the grown cells in the same manner as in (1). TA108 strain was transformed with the plasmid thus obtained in the same manner as in (3), and the kanamycin-resistant colonies grown on RCGP agar medium containing 200 µg/ml kanamycin were scraped up, and washed twice with physiological saline solution by centrifugation. The washed cells were spread on minimal agar medium M1 containing 3 mg/ml 5FT, and cultured at 30° C. for three days. From the grown colonies were selected those which are capable of growing on M1 agar medium containing 3 mg/ml 5FT and on NB agar medium containing 10 µg/ml kanamycin. A plasmid isolated from one of the selected strains was named pCtrp57.

AS activities of *Corynebacterium glutamicum* ATCC 13032 and TA108 strains carrying pCtrp1 or pCtrp57 were determined according to the method of H. Hagino, et al. [Agric. Biol. Chem., 39, 323 (1975)], and their PRT activities were determined according to the method of J. Ito and C. Yanofsky [J. Biol. Chem., 97, 734 (1969)]. AS and PRT activities of TA108 strains carrying pCtrp1 or pCtrp57 were more than 10 times as high as those of ATCC 13032 strain. Tryptophan concentrations for 50% inhibiting the AS activities of ATCC 39019 strain, TA108 strain carrying pCtrp1 and TA108 strain carrying pCtrp57 were 0.002 mM, 0.008 mM and 4.0 mM, respectively, while tryptophan concentrations for 50% inhibiting the PRT activities of these three strains were 0.19 mM, 0.19 mM and 4.8 mM, respectively. This indicates that AS and PRT encoded by pCtrp57 are less sensitive to tryptophan by a factor of about 500 and about 25, respectively, compared with AS and PRT encoded by pCtrp1.

(5) Sub-cloning of a DNA fragment containing all of genetic information relating to the synthesis of AS, PRT, PRAI, InGPS and TS in pCGDSI:

To 100 µl of reaction solution Y-100 containing 5 µg of pCtrp57 plasmid DNA was added 0.5 unit of BglII, and the mixture was subjected to reaction at 37° C. for ten minutes to effect partial digestion. The DNA fragment of 7.5 Kb thus formed was isolated from agarose gal [Molecular Cloning, 164 (1982)]. Separately, 5 units of BglII was added to 100 μl of reaction solution Y-100 containing 3 μg of pCGDS1 plasmid DNA, and the mixture was subjected to reaction at 37° C. for 60 minutes. The reaction was stopped by treatment with phenol. Both reaction mixtures thus obtained were mixed, and twice as much ethanol as the mixture by volume was added to precipitate DNA. The DNA was recovered and suspended in 200 μl of water.

To 200 μl of the DNA suspension were added 40 μl of buffer solution for T4 ligase at a 10-fold concentration, 40 μl of 5 mM ATP, 300 units of T4 ligase and 120 μl of water, and the mixture was subjected to reaction at 12° C. for 16 hours.

The reaction mixture was used for transformation of TA108 strain in the same manner as in (3).

The spectinomycin-resistant colonies grown on RCGP agar medium containing 400 μg/ml spectinomycin were scraped up, and washed twice with physiological saline solution by centrifugation. The washed cells were suspended in 1 ml of physiological saline solution. The cell suspension was spread on minimal agar medium M1 containing 3 mg/ml PFP and 100 μg/ml spectinomycin, and cultured at 30° C. for three days. From the grown colonies were selected transformants resistant to PFP and spectinomycin and not requiring tryptophan. Plasmid DNAs were isolated from these transformants in the same manner as in (1). Digestion with various restriction enzymes and analysis by agarose gel electrophoresis revealed that the plasmid DNA isolated from one of the transformants and named pCDtrp157 has a structure in which two BglII-cleaved DNA fragments of 4.5 Kb and 3.0 Kb have been inserted into the BglII cleavage site on pCGDS1 (refer to FIG. 1).

In order to confirm the presence of all of genetic information relating to the synthesis of AS, PRT, PRAI, InGPS and TS, plasmid pCDtrp157 was subjected to the partial digestion with BglII in the same manner as above, and a DNA fragment of 7.5 Kb was isolated from agarose gel, which was then ligated with pCE53 previously cleaved with BamHI. The product was used for transformation of TA108 strain in the same manner as above, and transformants resistant to kanamycin and not requiring tryptophan were selected. Digestion with various restriction enzymes and analysis by agarose gel electrophoresis revealed that the plasmid DNA isolated from one of the transformants and named pCtrp577 has a structure in which two BglII-cleaved DNA fragments of 4.5 Kb and 3.0 Kb have been inserted into the BamHI cleavage site on pCE53. Identification of the genes relating to the tryptophan biosynthesis was carried out in the same manner as in (3) using pCtrp577, whereby it was confirmed that all of genetic information relating to the synthesis of AS, PRT, PRAI, InGPS and TS is located on the 7.5 Kb DNA fragment inserted into the BamHI cleavage site on pCE53.

(6) Production of L-tryptophan by strains carrying pCGDS1, pCtrp57 or pCDtrp157:

Seed cultures (4 ml each) of *Corynebacterium glutamicum* ATCC 21854, which does not produce L-tryptophan and requires phenylalanine and tyrosine and *Corynebacterium glutamicum* BPS-13 (FERM BP-1777), which is a mutant sensitive to 3-bromopyruvic acid and derived from ATCC 21851 strain, were respectively inoculated into 40 ml of SSM medium containing 50 μg/ml each of phenylalanine and tyrosine, and Cultured with shaking at 30° C. When OD reached 0.2, treatment with penicillin G was carried out in the same manner as in (1), and culturing was further continued until OD reached 0.6. The grown cells were collected and treated with lysozyme in the same manner as in (2), and the resulting protoplasts were transformed in the same manner as in (2) using pCGDS1, pCtrp57 or pCDtrp157. Plasmid DNAs were isolated from the kanamycin- or spectinomycin-resistant transformants thus obtained in the same manner as in (1), and their structures were analyzed by digestion with various restriction enzymes. It was confirmed that these transformants carry pCGDS1, pCtrp57 or pCDtrp157. Of these, ATCC 21854 strain carrying pCDtrp157 was deposited with FRI under the Budapest Treaty on April 9, 1988 as *Corynebacterium glutamicum* K-76 (FERM BP-1847).

L-tryptophan production test by test-tube culture was carried out with the above transformants and their respective parent strains as described below.

Each strain was cultured with shaking in 3 ml of S1 medium (20 g/l glucose, 15 g/l polypeptone, 15 g/l yeast extract, 2.5 g/l NaCl, 1 g/l urea, 200 mg/l L-tyrosine and 200 mg/l L-phenylalanine; pH 7.2) at 30° C. for 24 hours. The resulting seed culture (0.5 ml) was inoculated into 5 ml of a production medium P1 [60 g/l glucose, 1 g/l $KH_2PO_4$, 1 g/l $K_2HPO_4$, 1 g/l $MgSO_4 \cdot 7H_2O$, 20 g/l $(NH_4)_2SO_4$, 10 g/l corn steep liquor, 10 mg/l $MnSO_4$, 30 mg/l biotin and 20 g/l $CaCO_3$; pH 7.2] in a large test tube. Shaking culture was carried out at 30° C. for 72 hours. For the culture of the transformants carrying pCGDS1 or pCDtrp157, 10 μg/ml streptomycin was added to the medium, and for the culture of the transformant carrying pCtrp57, 10 μg/ml kanamycin was added. After the culturing was finished, the culture filtrate was subjected to high performance liquid chromatography (HPLC) by the o-phthalaldehyde/2-mercaptoethanol-postcolumn derivatization method to determine the amount of L-tryptophan formed. The results are shown in Table 1.

TABLE 1

| Strain | L-tryptophan (g/l) |
| --- | --- |
| ATCC 21854 | 0 |
| ATCC 21854/pCGDS1 | 0 |
| ATCC 21854/pCtrp57 | 3.5 |
| K76 (ATCC 21854/pCDtrp157) | 5.6 |
| BPS-13 | 7.5 |
| BPS-13/pCGDS1 | 8.2 |
| BPS-13/pCtrp57 | 9.6 |
| BPS-13/pCDtrp157 | 11.0 |

(7) Culture test using a 2-liter jar fermentor

A culture test using a 2-liter jar fermentor was carried out with BPS-13 and BPS-13/pCDtrp157 strains in the following manner.

Each strain was cultured with shaking in 20 ml of S1 medium at 30° C. for 24 hours. Then, 10 ml of the first seed culture obtained was inoculated into 120 ml of S2 medium [50 g/l sucrose, 2 g/l $KH_2PO_4$, 0.5 g/l $MgSO_4 \cdot 7H_2O$, 5 g/l $(NH_4)_2SO_4$, 1 g/l urea, 10 mg/l $FeSO_4 \cdot 7H_2O$, 10 mg/l $MnSO_4 \cdot 4-6H_2O$, 4 mg/l $CuSO_4 \cdot 5H_2O$, 40 g/l corn steep liquor, 222 mg/l L-tyrosine, 362 mg/l L-phenylalanine, 50 μg/l biotin, 100 μg/l thiamine hydrochloride and 20 g/l $CaCO_3$; pH 7.2] in a 1-liter Erlenmeyer flask. Shaking culture was carried out at 30° C. for 24 hours. Then, 120 ml of the second seed culture obtained was inoculated into 550 ml of a production medium J1 [63 g/l sucrose, 2 g/l $KH_2PO_4$, 1.2 g/l $K_2HPO_4$, 1.7 g/l $MgSO_4 \cdot 7H_2O$, 17 g/l $(NH_4)_2SO_4$, 13 mg/l $FeSO_4 \cdot 7H_2O$, 13 mg/l $MnSO_4 \cdot 4-6H_2O$, 6 mg/l $CuSO_4 \cdot 5H_2O$, 66 g/l corn steep liquor, 310 mg/l L-tyrosine, 650 mg/l L-phenylalanine, 230 μg/l biotin and 450 μg/l thiamine hydrochloride; pH 6.8] in a 2-liter jar fermentor.

Culturing was carried out at 30° C. with aeration (1 vvm) and agitation (800 rpm) while maintaining the pH at 6.1 by addition of aqueous ammonia. For the culture of BPS 13/pCDtrp157 strain, 10 μg/ml streptomycin was added to the medium. A feed medium (205 ml) [374 g/l sucrose, 0.7 g/l $KH_2PO_4$, 0.5 g/l $K_2HPO_4$ and 600 mg/l L-tyrosine] was added twice during the course of culturing, which was continued until the sugar was completely consumed. After the culturing was finished, the culture was diluted 1:100 with water and heated at 60° C. for five minutes, and the culture filtrate was subjected to HPLC by the o-phthalaldehyde/2-mercaptoethanol-postcolumn derivatization method to determine the amount of L-tryptophan formed. The results are shown in Table 2.

TABLE 2

| Strain | L-tryptophan (g/l) |
|---|---|
| BPS-13 | 20.1 |
| BPS-13/pCDtrp157 | 32.6 |

What is claimed is:

1. A recombinant DNA carried by *Corynebacterium glutamicum* K76 (FERM BP-1847), wherein said recombinant DNA is pCDtrp157.

2. A microorganism belonging to the species *Corynebacterium glutamicum,* said microorganism carrying recombinant DNA which is pCDtrp157.

3. A microorganism according to claim 2, wherein said microorganism is *Corynebacterium glutamicum* K76 (FERM BP-1847).

4. A process for producing L-tryptophan which comprises the steps of: culturing in a culture medium a microorganism belonging to species *Corynebacterium glutamicum,* said microorganism carrying a recombinant DNA which is pCDtrp157;

accumulating L-tryptophan in the culture medium; and recovering L-tryptophan from the culture medium.

5. A process according to claim 4, wherein said microorganism is *Corynebacterium glutamicum* K76 (FERM BP-1847).

* * * * *

UNITED STATES PATENT AND TRADEMARK OFFICE
CERTIFICATE OF CORRECTION

PATENT NO. : 5,563,052
DATED : October 8, 1996
INVENTOR(S) : RYOICHI KATSUMATA ET AL.    Page 1 of 3

It is certified that error appears in the above-identified patent and that said Letters Patent is hereby corrected as shown below:

Title page,
item [73] ASSIGNEE

"LTD," should read --Ltd.,--.

Title page,
item [56] REFERENCES CITED

Other Publications,
Line 6, "E. Tribe" should read --D. Tribe--,
Line 7, "Escherchia" should read --Escherichia--,
Line 10, "1982," should read --1981--, and
Line 11, "Eschericha" should read --Escherichia--.

COLUMN 2

Line 45, "glutamicum" should read
--glutamicum ATCC 13032--.
Line 46, "ATCC 13032" should be deleted.

COLUMN 3

Line 44, "routants" should read --mutants--.

COLUMN 4

Line 26, "the-preparation" should read
--the preparation--.

UNITED STATES PATENT AND TRADEMARK OFFICE
CERTIFICATE OF CORRECTION

PATENT NO. : 5,563,052

DATED : October 8, 1996

INVENTOR(S) : RYOICHI KATSUMATA ET AL.　　Page 2 of 3

It is certified that error appears in the above-identified patent and that said Letters Patent is hereby corrected as shown below:

COLUMN 5

Line 29, "so" should read --so- --.

COLUMN 6

Line 42, "0D" should read --OD--.
Line 48, "0,005M" should read --0.005M--.

COLUMN 7

Line 28, "laurylsulfate" should read --lauryl sulfate--.

COLUMN 8

Line 57, "50 mg/l" should read --50 μg/l--.

COLUMN 9

Line 34, "for" should be deleted.

UNITED STATES PATENT AND TRADEMARK OFFICE
CERTIFICATE OF CORRECTION

PATENT NO. : 5,563,052
DATED : October 8, 1996
INVENTOR(S) : RYOICHI KATSUMATA ET AL.

It is certified that error appears in the above-identified patent and that said Letters Patent is hereby corrected as shown below:

<u>COLUMN 11</u>

Line 3, "gal" should read --gel--.

Signed and Sealed this

First Day of July, 1997

Attest:

Attesting Officer

BRUCE LEHMAN

Commissioner of Patents and Trademarks